(12) United States Patent
Prater et al.

(10) Patent No.: US 10,557,789 B2
(45) Date of Patent: Feb. 11, 2020

(54) NANOSCALE INFRARED SPECTROSCOPY WITH MULTI-FREQUENCY ATOMIC FORCE MICROSCOPY

(71) Applicant: Bruker Nano, Inc., Santa Barbara, CA (US)

(72) Inventors: Craig Prater, Santa Barbara, CA (US); Kevin Kjoller, Santa Barbara, CA (US); Doug Gotthard, Santa Barbara, CA (US); Qichi Hu, Camarillo, CA (US)

(73) Assignee: Bruker Nano, Inc., Santa Barbara, CA (US)

( * ) Notice: Subject to any disclaimer, the term of this patent is extended or adjusted under 35 U.S.C. 154(b) by 0 days.

(21) Appl. No.: 13/956,156

(22) Filed: Jul. 31, 2013

(65) Prior Publication Data
US 2015/0034826 A1 Feb. 5, 2015

(51) Int. Cl.
*G01N 21/63* (2006.01)
*G01N 21/35* (2014.01)

(52) U.S. Cl.
CPC .................. *G01N 21/35* (2013.01)

(58) Field of Classification Search
CPC .. G01N 21/35; G01N 21/359; G01N 21/3504; G01J 3/02; G01J 3/42
See application file for complete search history.

(56) References Cited

U.S. PATENT DOCUMENTS

| | | | | |
|---|---|---|---|---|
| 6,584,413 | B1 * | 6/2003 | Keenan | G01J 3/28 702/194 |
| 8,739,309 | B2 * | 5/2014 | Hu | B82Y 35/00 850/1 |
| 2003/0103552 | A1 * | 6/2003 | Chi et al. | 374/137 |
| 2010/0045970 | A1 * | 2/2010 | Raschke | 356/51 |
| 2011/0058248 | A1 * | 3/2011 | Vodopyanov et al. | 359/330 |
| 2011/0061452 | A1 * | 3/2011 | King et al. | 73/105 |
| 2012/0252058 | A1 * | 10/2012 | Cohen et al. | 435/34 |
| 2013/0036521 | A1 * | 2/2013 | Prater | B82Y 35/00 850/56 |
| 2014/0289912 | A1 * | 9/2014 | Andreev | B82Y 35/00 850/18 |

OTHER PUBLICATIONS

Widjaja et al. "Band-Target Entropy Minimization (BTEM) Applied Hyperspectral Raman Image Data" Society for Applied Spectroscopy, vol. 57, No. 11, 2003, p. 1353-1362.*

* cited by examiner

*Primary Examiner* — David P Porta
*Assistant Examiner* — Mamadou Faye
(74) *Attorney, Agent, or Firm* — Boyle Fredrickson S.C.

(57) ABSTRACT

Described are techniques for obtaining spectroscopic information from sub-micron regions of a sample using a probe microscope. The current invention uses the response of an AFM cantilever at a plurality of frequencies to substantially reduce the impact of background absorption away from the sub-micron region of interest. This innovation substantially improves the quality of spectra for top down illumination of samples that are not suitable for bottoms up illumination of the prior art.

24 Claims, 8 Drawing Sheets

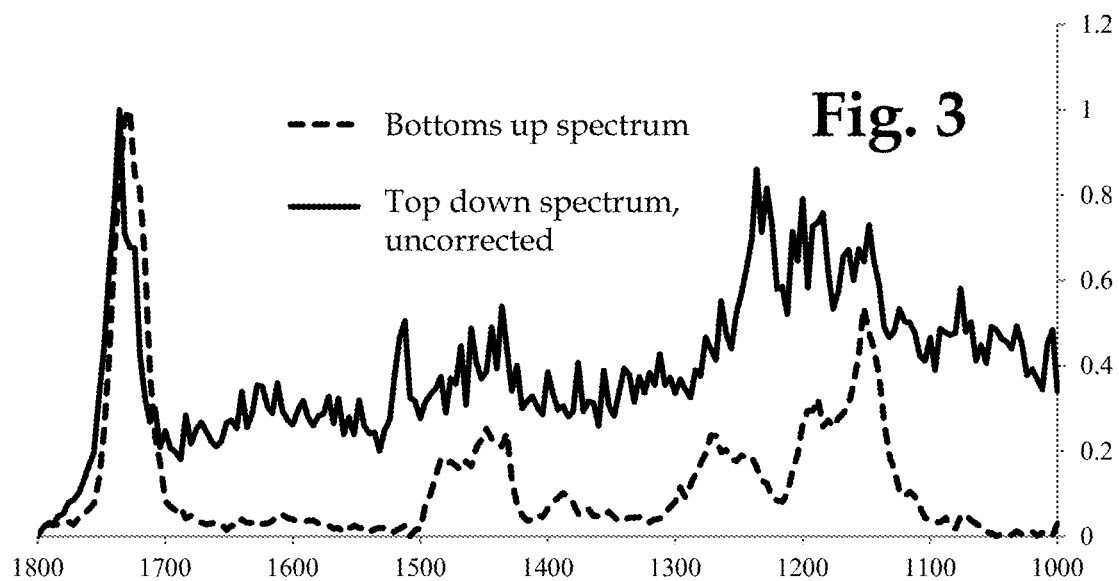
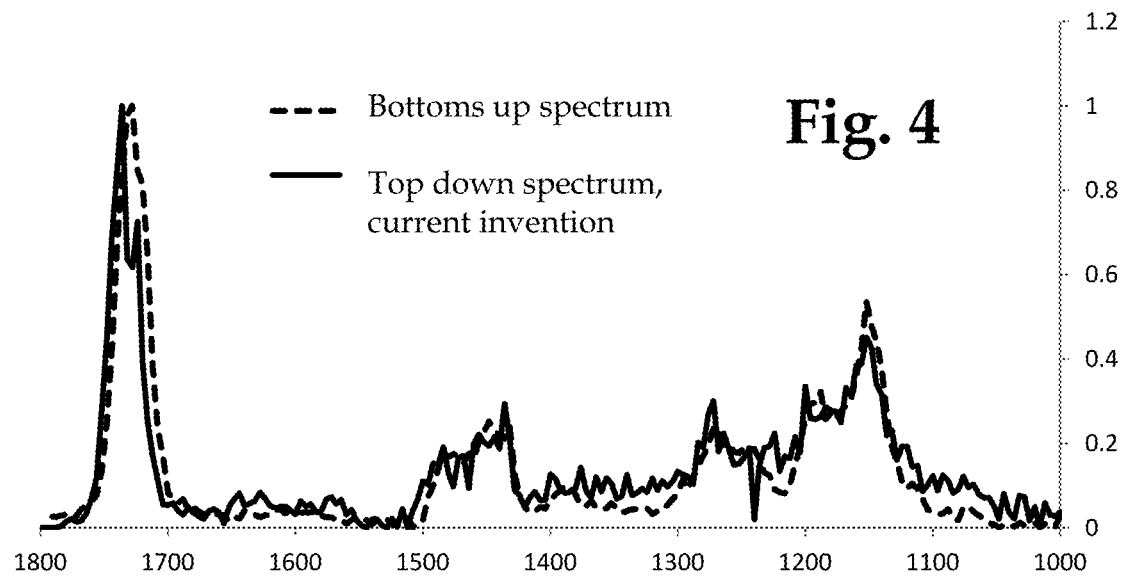

NANOSCALE INFRARED SPECTROSCOPY WITH MULTI-FREQUENCY ATOMIC FORCE MICROSCOPY

STATEMENT REGARDING FEDERALLY SPONSORED RESEARCH OR DEVELOPMENT

This invention was made with governmental support under NSF SBIR 1126871 awarded by the National Science Foundation. The government has certain rights in the invention.

BACKGROUND OF THE INVENTION

This invention relates to nanoscale infrared spectroscopy using Atomic Force Microscope based techniques and particularly to isolating tip dependent signals from background signals.

In recent years atomic force microscopy has intersected with infrared spectroscopy to provide spectroscopic characterization of materials with sub-micron spatial resolution. One commonly used technique is called Photo-Thermal Induced Resonance, as described by Dazzi et al in U.S. Pat. Nos. 8,001,830 and 8,402,819 and related applications, each incorporated by reference. In this technique a pulsed, tunable infrared source is used to illuminate a region of a sample. When the source is tuned to a wavelength corresponding to an absorption of the sample, a portion of the incident radiation is absorbed by the sample, rapidly heating the absorbing region. The rapid temperature rise creates a corresponding thermal expansion shock wave that produces a transient force on the tip of an AFM cantilever probe. The AFM cantilever then rings at one or more frequencies, corresponding to the contact resonance modes of the AFM cantilever. By measuring the amplitude of the cantilever response as a function of illumination wavelength, it is possible to create an absorption spectrum of regions of the sample.

In certain implementations of this technique, see FIG. 1, the sample 104 is mounted to a prism 106 which is illuminated by IR radiation 108, creating absorption induced oscillation of cantilever 100 due to sample expansion at tip 102. For this case, the prism 106 is chosen such that radiation 108 is totally contained within the prism 106 and sample 104 by total internal reflection. Thus there is essentially no radiation on the tip 102 and cantilever 100.

The implementation of FIG. 1 is advantageous in that it restricts the illumination to just the sample 104. However not all samples of interest are small enough or of the proper configuration or transparency to be mountable on a prism and illuminated from the bottom. An alternative, more generally applicable implementation is shown in FIG. 2. In this case, sample 204 is illuminated from the top by IR radiation 208. It should be noted that the figure is schematic and not drawn to scale. Tip apex 203 is very small compared to the minimum spot size achievable for the IR illumination. Thus illumination 208 illuminates the sample 204 in the region of the tip apex 203, but also illuminates the sample (and/or sample mount) away from the tip apex as well as the tip shank 202 and a portion of the cantilever 200. These other areas illuminated can affect the spatial resolution which can be compromised by at least two background sources in particular: (1) absorption of light by the cantilever and/or tip away from the tip apex; and (2) absorption of light by the sample, but in an area away from the tip apex. Both of these responses add to the total cantilever response. The resulting measured absorption spectra can then be heavily contaminated by these background signals, often obscuring the signal from the much smaller volume of sample material under the tip apex 203.

There is a large class of samples, which we will define as "in situ" samples, where bottoms up illumination is not suitable. These in situ samples are generally better measured in top-side illumination. For these samples the background problem is especially significant. In situ samples are samples that by their nature generally cannot be prepared for placement on an infrared transparent prism for bottoms up illumination. These include samples that are opaque over a wavelength range of interest and thus cannot be used for total internal reflection illumination from below. In situ samples also include samples where the regions of interest are on a predefined substrate, for example a defect or a thin film on a semiconductor wafer. Other examples include geological/petrochemical samples, wear tracks, substrates and devices used in data storage, coatings and deposited thin films, and similar samples. In situ samples can also include samples that cannot be readily prepared into thin sections on an infrared transparent prism, for example samples that cannot be readily microtomed, drop cast or spun cast. These can be samples that may be too hard and/or fragile to cut into thin sections (<1 µm thickness). Other examples can include pharmaceutical samples and powders that tend to crumble when cut. For this family of in-situ samples that cannot be readily measured in bottoms up illumination, top side illumination is highly desirable. But with topside illumination, the background absorption from the light incident on the cantilever and/or tip signals can significantly undermine the quality of the measured absorption spectra and can also significantly degrade the spatial resolution of the measurement.

An example of this excessive background is shown in FIG. 3. This figure shows two AFM-IR spectra obtained on a sample of poly-methylmethacrylate (PMMA). The dashed curve is taken in the bottoms up illumination scheme of FIG. 1 and fairly accurately reflects the absorption properties of the PMMA material. The solid curve shows a measurement obtained on the same sample, but using top side illumination. The spectrum clearly shows a significant increase in background absorption, obscuring much of the detail of the actual absorption properties of the PMMA material. The current invention details techniques for substantially reducing this background effect to allow more accurate nanoscale spectroscopic measurements, even with top-side illumination. A significant problem is that for unknown samples, which is of course what the PTIR technique is intended to identify, sometimes the background contribution to the spectra is larger than the signal from the tip signal, so it can be difficult to accurately measure the tip signal, and thus the true sample absorption spectra.

SUMMARY OF THE INVENTION

To overcome the limitations of the prior art, the inventors have developed a technique to rapidly construct nanoscale absorption spectra that separate the background absorption from the region of interest absorption. The current invention simultaneously measures and records the probe response at a plurality of frequencies, preferably corresponding to the different cantilever oscillation modes, in response to absorption of infrared radiation. The probe responses at the plurality of frequencies are then combined to calculate separate spectra for background sources and for the sample region of interest. In a preferred embodiment the probe responses are measured at a plurality of contact resonance frequencies (often five or more frequencies) which are then analyzed to extract sample signal and background components.

The inventors realized that such a decomposition into signal and background is possible because the fractional contribution (weighting) of the background and signal varies as a function of frequency, and specifically for each cantilever mode. For example the fundamental cantilever mode has a very large contribution of background, while higher modes have less (but non-zero) background fraction. The fact that each mode has a different background to signal ratio allows the application of multivariate statistical analysis to reconstruct the underlying spectral components that make up the measured probe response.

An example of a reconstructed absorption spectrum with the unwanted background absorption substantially suppressed is shown in FIG. 4 (solid curve). This measurement was performed in top down illumination, normally very susceptible to background contamination, as was shown in FIG. 3. In the case of the current invention, however, the reconstructed absorption spectrum is largely uncontaminated by background absorption and matches well to the conventional bottoms up spectrum (dashed curve).

While many different multivariate analysis techniques can be applied, one technique that is well suited is multivariate curve resolution (MCR). A good review of MCR can be found at the website: http://www.mcrals.info/. This technique assumes that a measured spectrum is a linear combination of component spectra multiplied by component weightings. While this technique by itself does not produce unique solutions, applying a series of real world constraints leads it to converge in many cases. Such constraints include that the component spectra cannot contain negative values (no negative absorption) and that the component weightings must be positive (no negative weightings). Other typically applied constraints are beyond the scope of this document, but are described in the above-referenced MCR website.

A key advantage of the MCR technique is that it is a blind reconstruction algorithm, i.e. it requires no input spectrum or assumed weighting for either component. This is especially suitable in the typical case where the details of the sample and background absorption are unknown. It is however possible to further improve the technique by providing known background spectra. Towards that end the inventors have also combined multifrequency measurements on the sample of interest with those on adjacent and nominally non-absorbing regions.

Without wishing to be bound by any particular theory, there can be discussion herein of beliefs or understandings of underlying principles relating to the analysis techniques used as part of the invention. It is recognized that regardless of the ultimate correctness of any mechanistic explanation or hypothesis, embodiments of the invention can nonetheless be operative and useful. Other multivariate statistical techniques that may be applied include self-modeling mixture analysis, spectral demixing, band target entropy minimization, alternating least squares, and other related techniques.

BRIEF DESCRIPTION OF THE DRAWINGS

FIG. 3 is a comparison of AFM-IR spectra on polymethylmethacrylate (PMMA) obtained in bottoms up illumination, in the method of FIG. 1, versus a spectrum obtained in top down illumination, the method of FIG. 2.

FIG. 4 is a demonstration of the ability of the current invention to substantially suppress the effects of background absorption, even with top side illumination. FIG. 4 specifically shows a multifrequency reconstructed spectrum under the current invention in top down illumination as compared to a conventional bottoms up spectrum.

DEFINITIONS

Figure 1:
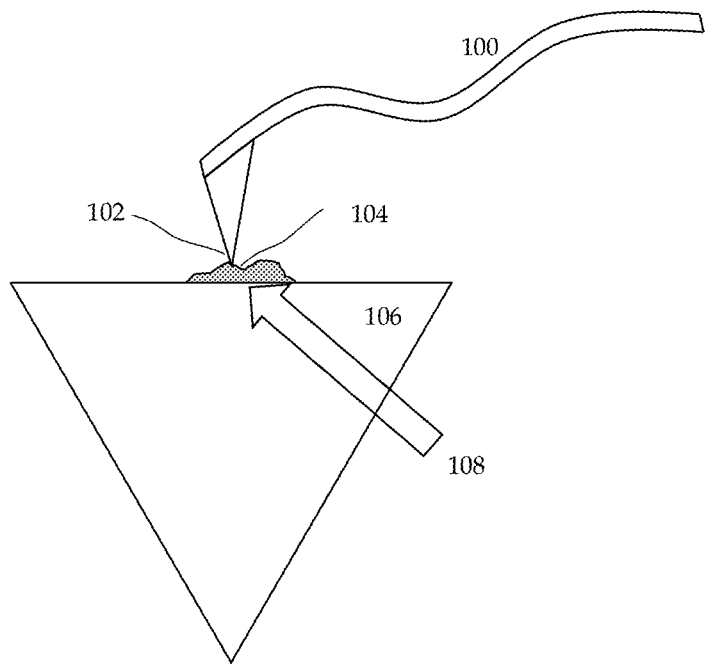
FIG. 1 is a simplified schematic diagram of the bottom up AFM-based IR spectroscopy technique called "Photo-Thermal Induced Resonance" (PTIR).
Figure 2:
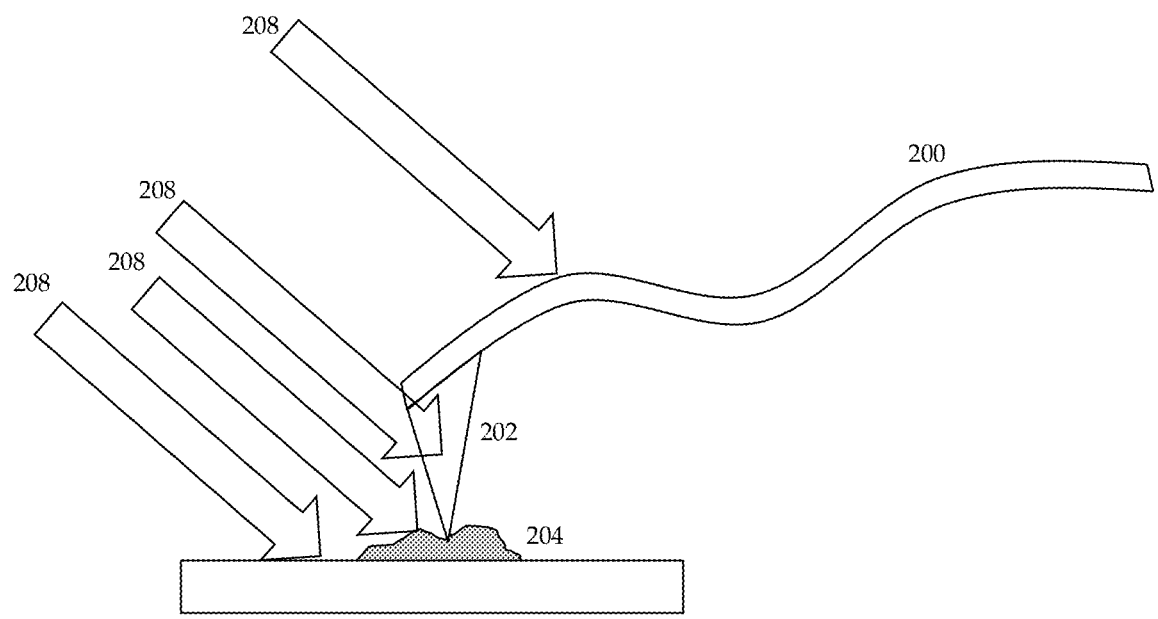
FIG. 2 is a simplified schematic diagram of the top down AFM-based IR spectroscopy technique called "Photo-Thermal Induced Resonance" (PTIR).

In general the terms and phrases used herein have their art-recognized meaning, which can be found by reference to standard texts, journal references and contexts known to those skilled in the art. The following definitions are provided to clarify their specific use in the context of the invention.

"Piezoelectric" refers to a material exhibiting a piezoelectric property. Piezoelectric properties include, but are not limited to, the ability to generate a voltage and/or a current upon the application of a mechanical stress and/or change of an applied mechanical stress. Piezoelectric properties include, but are not limited to, the ability to change physical dimensions and/or the state of strain upon the application of a voltage and/or a current.

"Sense" and "sensing" refer to determination and/or observation of a signal indicative of a value, variable and/or property. In some embodiments, sensing refers to direct measurement of a value, variable and/or property; in other embodiments, sensing requires transformation (e.g., a mathematical transformation) to convert one value, variable and/or property into a measured and/or detected value.

"Measure" and "measuring" refer to determination of an absolute or relative value of a variable and/or property.

"Detect" and "determine" refer to observation and/or measurement of a property, object or value and/or a change in a property, object or value.

"Deflection" refers to motion of one object, such as a bending or elastic deformation. Deflection may comprise static motion, transient motion and/or vibrational motion, for example due to a force and/or the presence of another object.

"Submicron region" refers to a portion of an object that has at least one characteristic dimension less than 1 micrometer. For example, a 900 nm spherical domain in a composite sample comprises a submicron region. Submicron regions may also be as small as a few nanometers or less. In some embodiments, a submicron region refers to the portion of an object or surface in contact with the tip of a microcantilever and that portion of the object or surface immediately surrounding the portion in contact with the tip.

"Contact mode" refers to a mode of operation of an atomic force microscope or microcantilever where the microcantilever tip is generally maintained in contact with a surface.

"Flexural mode" refers to a characteristic vibrational bending mode of a microcantilever which oscillates at a characteristic frequency. A flexural mode can refer to the first order or a higher vibrational mode of a microcantilever. "Contact mode flexural mode" refers to a characteristic vibrational mode of a microcantilever having a tip which is maintained in contact with a surface. The contact mode flexural modes and the free flexural modes (non-contact flexural modes) of a microcantilever are generally different and oscillate with different characteristic frequencies. In some embodiments, a contact flexural mode depends on the mechanical properties of the sample that is in contact with the tip of a microcantilever.

"Quality factor" or "Q" refers to a measure of the sharpness of an oscillatory resonance, for example a flexural oscillation of a cantilever. The Quality factor is generally defined to be the resonant frequency divided by the width of the resonance at half the maximum energy, i.e. $Q=f_0/\Delta f$.

"Substantially independent" refers to the ability of one object to behave, move, or otherwise perform a function without being affected by or with reduced effects from another object.

"Substantially within" refers to containment of one object within the bounds of another object.

"Spatially resolved map" refers to a spatial plot showing position dependent variations, for example position dependent variations in a property.

"Interacting a probe tip . . . with a sample" refers to positioning the probe tip of a cantilever probe in sufficient proximity with a surface such that it can sense and/or induce a force between the probe tip and the a sample. Such interaction can be attractive, repulsive, or a combination of both. The interaction forces can include but are not limited to coulomb repulsion, Van der Waals, electrostatic, meniscus, hydrophobic, and others. The probe-tip interaction can be continuous contact, intermittent contact, tapping, non-contact, modulated force, and/or pulsed force, for example.

DETAILED DESCRIPTION OF THE INVENTION

Figure 5A:
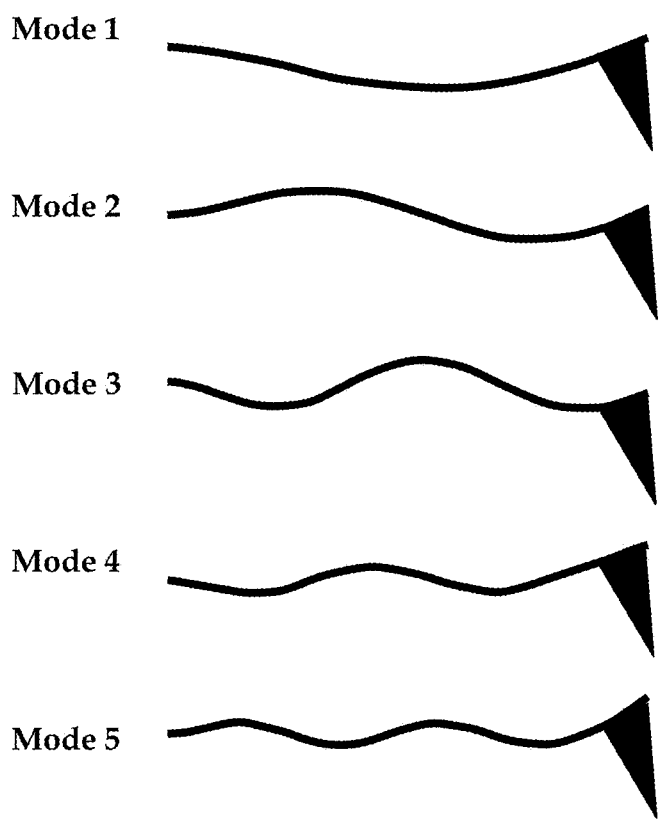
FIG. 5A illustrates cantilever modes of oscillation for contact resonances excited by infrared absorption.

The current invention is focused on obtaining absorption spectra of sub-micron regions of a sample, while substantially suppressing effects from background absorption from other regions of the sample and absorption from the AFM probe away from the AFM tip apex. A key to achieving this goal is to measure the probe response to IR absorption at a plurality of cantilever oscillation frequencies and using the differential response at multiple frequencies to calculate separate background absorption from the absorption of the sub-micron region of the sample. In one embodiment the cantilever motion is measured at multiple frequencies corresponding to oscillation modes of the cantilever. An example of such cantilever modes are illustrated schematically in FIG. 5A. The modes illustrated are so called "contact resonance" modes in which the AFM is operated in contact mode. These oscillation modes correspond to conditions where the tip of the AFM is constrained to some degree by contact between the tip and sample. Alternate modes that can be used are free resonance modes and/or tapping mode resonances. In these cases the cantilever oscillates such that it intermittently interacts with the sample surface.

Figure 5B:
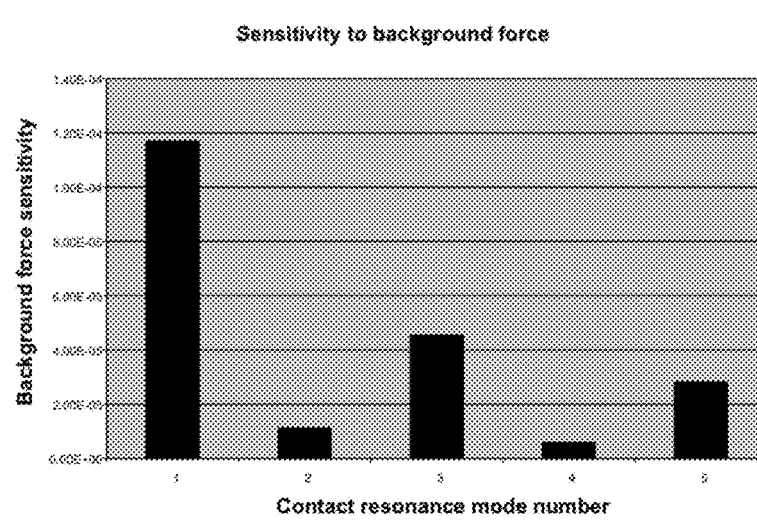
FIG. 5B illustrates a model for the varying sensitivity to the background effects for different cantilever oscillation modes in one mode of background forces.

The current invention can achieve separation between background absorption and sample absorption due to the fact that the relative cantilever response to background and sample changes as a function of frequency. This is illustrated schematically in FIG. 5B for one model of background absorption. In this model uniform background force was applied over the entire cantilever. For higher order modes of oscillation, the mode shape consists of part of the cantilever deflecting upwards and part downwards. The background forces that act along the entire cantilever tend to be averaged out to some degree for these higher modes, reducing their sensitivity to unwanted forces. And specifically, symmetric modes of oscillation, for example the 2nd, 4th, 6th, and higher even number modes are most effective at reducing sensitivity to this background. Note that each cantilever mode has a unique sensitivity to the background force. In practice, the actual sensitivity of each mode to background absorption depends on the spatial and temporal nature of the background force and will not always have the characteristics of FIG. 5B. But in general each cantilever oscillation mode will have a different response to background absorption.

Figure 6:
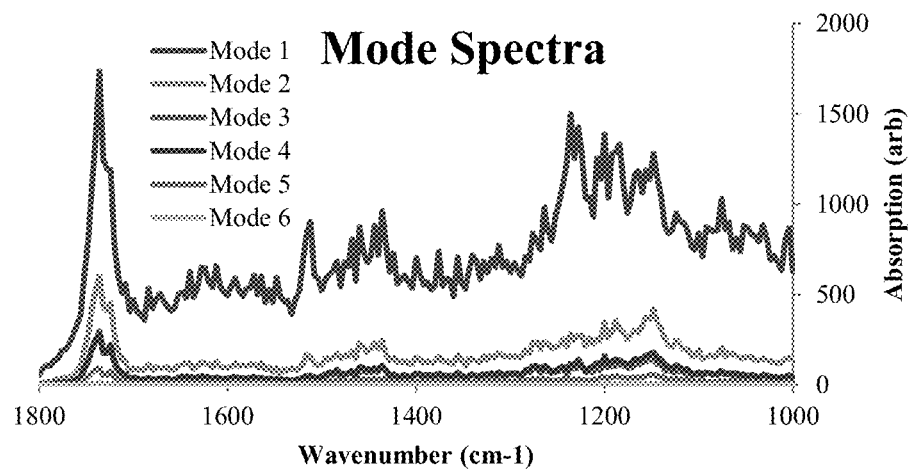
FIG. 6 shows examples of PTIR absorption spectra on a sample of poly-methyl methacrylate (PMMA) at a plurality of frequencies.
Figure 7A:
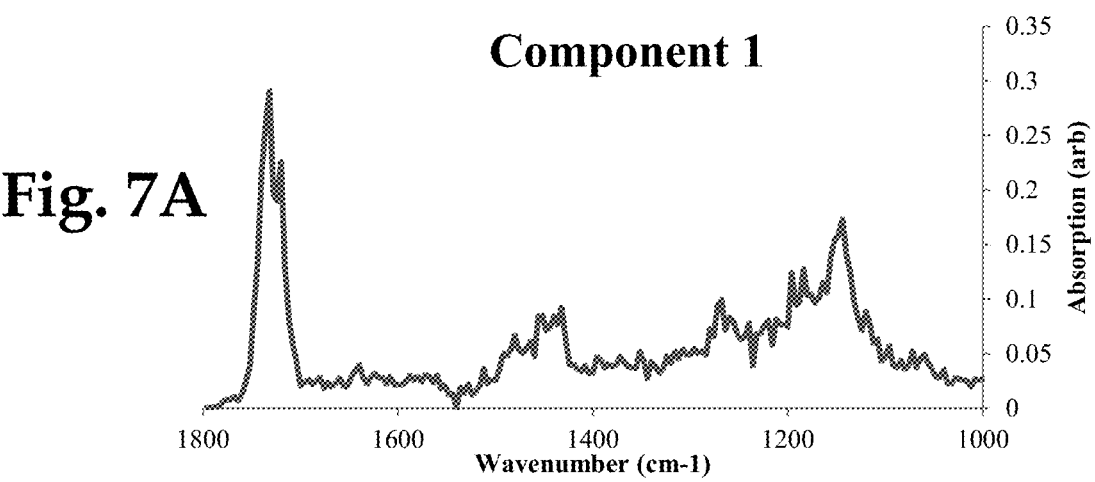
FIGS. 7A and 7B illustrate a sample absorption spectrum (7A) and background absorption spectrum (7B) reconstructed from the multi-frequency spectra in FIG. 6.
Figure 7B:
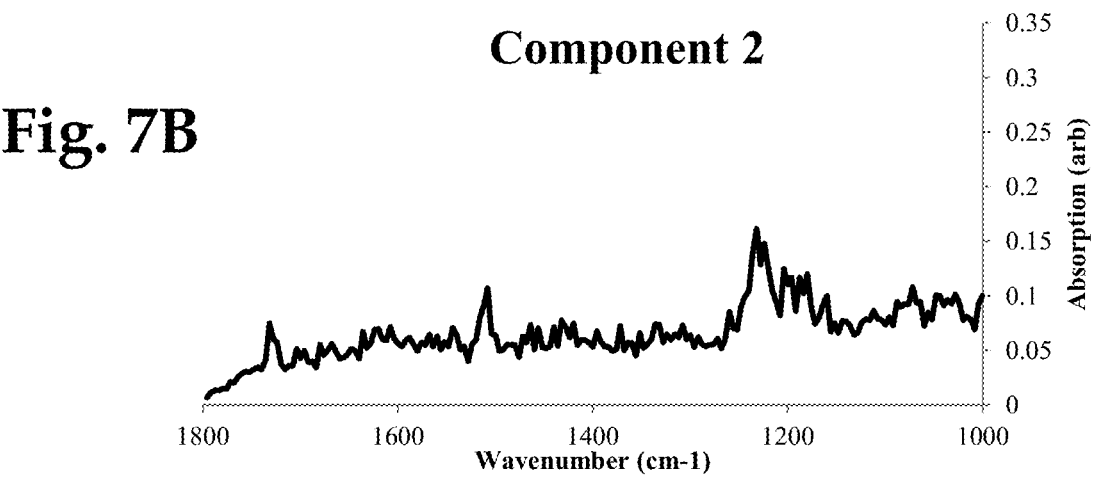
Figure 8:
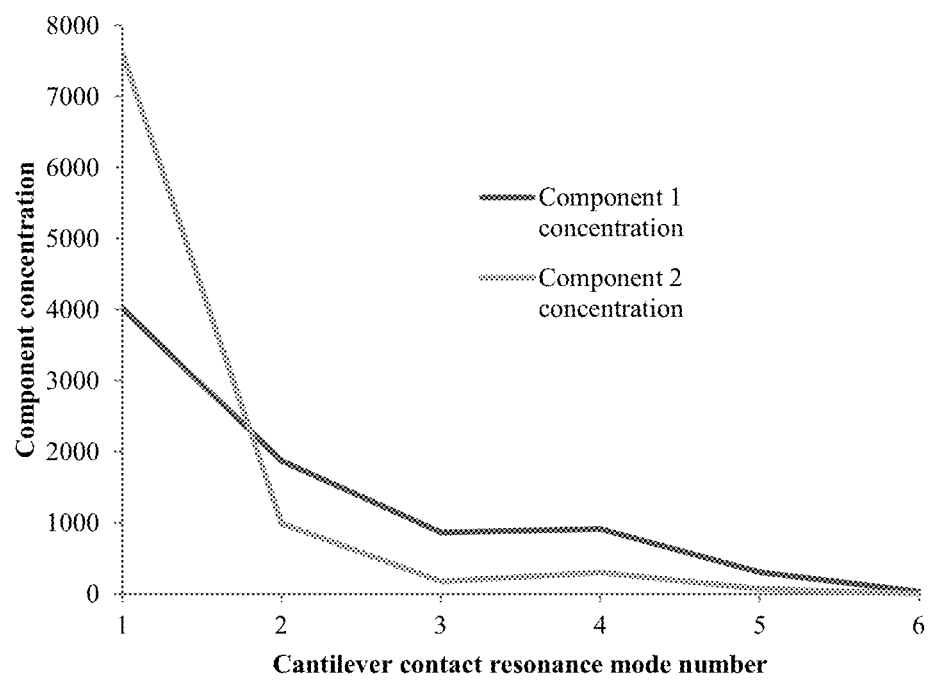
FIG. 8 shows the contribution of sample absorption (component 1) and background absorption (component 2) as a function of cantilever oscillation mode as determined by multivariate curve resolution.

FIG. 6 shows absorption spectra for the first six cantilever oscillation modes, obtained on a sample of PMMA with top side illumination. FIGS. 7A and 7B illustrate the reconstruction of two separate spectra from this multi-frequency data. FIG. 7A is a reconstruction of the sample spectrum, i.e. the absorption from a sub-micron region of the sample under the tip apex. FIG. 7B shows reconstruction of the background absorption, i.e. the combined absorption of all background sources included absorption by the AFM tip and cantilever away from the tip apex and regions of the sample away from the tip apex.

In the next section we describe techniques for combining absorption measurements at different cantilever frequencies to separate spectra into background and sample absorption as illustrated in FIGS. 7A-B. The starting point is to assume that each measured spectrum at each individual cantilever oscillation mode is a linear combination of sample and background absorption with different weighting factors.

For example, for a given cantilever mode n, the total detected signal may be modeled as:

$$S_n(\lambda)=a_n A(\lambda)+b_n B(\lambda); \quad\quad\quad (Eq.1)$$

where $S_n(\lambda)$ is the total signal as a function of radiation wavelength, $A(\lambda)$ and $B(\lambda)$ are the tip and background signals respectively, and $a_n$ and $b_n$ are the weighting factors for the tip and background contribution to the total for each mode n. The signal $S_n(\lambda)$ can then be measured for a series of cantilever oscillation modes n. The component spectra $A(\lambda)$ and $B(\lambda)$ are the same for all modes, but the weighting coefficients $a_n$ and $b_n$ will be different for each mode, as described below. The inventors realized that certain multivariate analytical techniques can be applied to solve problems of the form of Eq. 1, even if neither the component spectra nor the weighting factors are known in advance. Specifically multivariate techniques exist that are intended for deconvolving component spectra for multicomponent mixtures. In these cases, a family of spectra are obtained for different concentrations of individual components or over spatial regions where the component concentrations vary. The multivariate demixing techniques then decompose the family of spectra at different concentrations or sample positions into component spectra and concentrations. The inventors realized that such multivariate demixing techniques could be applied instead to families of spectra obtained simultaneously on the same region of the sample allowing the creation of absorption spectra of sub-micron regions of a sample, substantially removing the influence of background absorption. Rapidly, efficiently, and even automatically removing the effects of background absorption from the cantilever and tip make top side illumination AFM-IR measurements far more practical. This invention therefore enables measurements on a substantially broader family of samples, including "in situ" samples described earlier, i.e. samples that are not amenable to bottoms up illumination.

The basic approach then is to deconvolve the set of spectra $S_n(\lambda)$ at different cantilever oscillation modes such that the background contribution $B(\lambda)$ can be separated from the signal contribution from the sub-micron region of interest $A(\lambda)$. The background contribution $B(\lambda)$ can comprise absorption from all other sources away from the tip apex. (The background can also be deconvolved into multiple components e.g $B(\lambda)$ and $C(\lambda)$, if desired.)

In the next section, we explain why it is possible to deconvole the set of spectra $S_n(\lambda)$ into sample and background components. The main reason for this is that each cantilever mode n has a different ratio of background and sample signal contribution. This results from the difference in the spatial distribution of the sample and background forces on an AFM cantilever. We now explain the origin of this difference.

In a simplified approximation, the cantilever end slope $S_n$ at the nth cantilever mode measured by the AFM in response to a transient force is given by:

$$S_n = \varphi'_n(\alpha L)\left[\int_0^L f(x, \omega)\varphi_n(x)dx\right]\frac{T(\omega)}{m\omega_n^2}; \quad \text{(Eq. 2)}$$

where $\varphi'_n(\alpha L)$ is the mode slope of the cantilever at the detector laser position $\alpha L$, where L is the length of the cantilever and $\alpha$ is the fractional length along the cantilever where the laser is positioned, $f(x,\omega)$ is the Fourier transform of the transient force applied to the cantilever as a function of position along the cantilever and frequency $\omega$, $\varphi_n(x)$ is the mode shape of the cantilever, and $T_n(\omega)$ is the cantilever transfer function (resonance response) for the nth mode, m is the cantilever mass and $\omega_n$ is the mode resonance angular frequency. Note that cantilever oscillations are excited by time varying forces, f(x,t) resulting from radiation incident on the cantilever and/or sample. The frequencies that get excited are determined by the Fourier transform $f(x,\omega)$ of the time varying force f(x,t) in combination with the cantilever transfer function $T_n(\omega)$, i.e. the cantilever's response as a function of frequency, including cantilever mode resonances. The time varying force can look largely like an impulse function, as in the case of a pulsed source, resulting in a Fourier transformed force $f(x,\omega)$ that has components at multiples of the pulse repetition rate. Alternately, in the case of a continuously modulated source, the Fourier transformed force can have components at the modulation frequencies. It is possible with either a pulsed or a modulated source to construct a pulse train and/or modulation profile that contains excitation frequencies at multiple cantilever oscillation modes, thus enabling measurements of spectroscopic responses at a plurality of cantilever frequencies.

To understand how multi-frequency analysis can help separate signal and background forces, we consider the bracketed term $\int_0^L f(x,\omega)\varphi_n(x)dx$. This term is the integral of the position and frequency dependent force $f(x,\omega)$ with the mode shape of the cantilever $\varphi_n(x)$. While the position dependence of force $f(x,\omega)$ is the same for every cantilever mode, the mode shape, $\varphi_n(x)$ varies dramatically from mode to mode. The net effect of this is that the mode shape $\varphi_n(x)$ acts as a weighting function in the integral of the force on the cantilever.

The force felt by the cantilever can be considered to be composed of two components:

$$f(x,\omega)=f_t(\omega)\delta(x-x_t)+f_b(x,\omega); \quad \text{(Eq. 3)}$$

The first term is the tip force and only applies a force to the cantilever at the tip location ($x=x_t$) and is zero everywhere else. By contrast the background force $f_b(x,\omega)$ is non-zero over a much larger area, roughly equivalent to the size of the light spot of incident radiation that overlaps with any part of the cantilever.

A key observation in this equation is that the changing mode shape alters the relative weighting of the tip force $f_t(\omega)$ vs. the background force $f_b(x,\omega)$. Thus the measured absorption spectra also vary as a function of mode, with different contributions of sample absorption and background. The result is a mode dependent variation in the fraction of the total signal that is composed by background absorption, as illustrated for one model of background absorption in FIG. 5B. The inventors realized that this different contribution of sample absorption and background as a function of cantilever mode provides an unanticipated method to decompose measured spectra into the separate components of sample and background.

To do this, we assume, as above, that the measured spectrum at a given mode is given by a linear combination of the absorption spectrum for each component (sample and background) times appropriate weighting factors:

$$S_n(\lambda)=a_n A(\lambda)+b_n B(\lambda)+e_n(\lambda); \quad \text{(Eq. 4)}$$

where $S_n(\lambda)$ is the cantilever deflection of the nth mode as a function of wavelength $\lambda$, $A(\lambda)$ is the absorption spectrum of sample material under the tip apex (the signal of interest), and $B(\lambda)$ is the background absorption spectrum from sources away from the tip apex. This $B(\lambda)$ can include optical absorption of the cantilever and/or tip, optical pressure, acoustic pressure waves from absorbing regions away from the tip apex and/or other non-local forces. The terms $a_n$ and $b_n$ are weighting factors that describe how much each component spectrum $A(\lambda)$ and $B(\lambda)$ contribute to the spectrum for each cantilever oscillation mode. These factors are different, with $b_n$ typically being largest for the $1^{st}$ mode and decreasing for higher modes. The term $e_n(\lambda)$ is a residual term, often noise, that is not modeled by the linear combination of the component spectra $A(\lambda)$ and $B(\lambda)$. Note that this approach can also be generalized to include multiple background components, for example a background component from cantilever/tip absorption and a separate background component for sample absorption from regions away from the tip apex.

Note that in some cases, especially in the presence of large background, it can be difficult to determine a priori which component in the multivariate demixing corresponds to the sample absorption spectrum and which component is the background. There are several approaches to deal with this type of ambiguity. One approach is to perform a measurement on a known sample with a generally known absorption spectrum. Choosing the demixed component spectrum with the best match to the known sample determines by process of elimination which demixed component corresponds to the background. Alternately, a measurement can be performed on a sample with minimal absorption, for example an infrared transparent substrate. In this case the absorption detected will belong primarily to the background absorption component. The key features of this background measurement, including any peaks, can be used to identify the background component on unknown samples. It is also possible to adjust the position of the incident beam of radiation such that it more fully covers the AFM cantilever and tip, in effect maximizing the background absorption. In this case either the larger component or the component that grows as the incident beam is realigned can be identified as the background component.

The cantilever deflection at the nth mode $S_n(\lambda)$ can be measured in a variety of ways. In the simplest implementation the cantilevers time varying deflection $z(t)$ can be Fourier transformed to determine the amplitude as a function of frequency $z(\omega)$. The amplitude at any given mode can be determined by evaluating $z(\omega)$ at $\omega=\omega_n$, where $\omega_n$ correspond to the nth cantilever oscillation mode. More accurate/lower noise results can be obtained by fitting a portion of the $z(\omega)$ response to a suitable curve, for example a parabola, Gaussian, or Lorentzian curve to extract the mode amplitude. Alternately, it is possible to use lock-in techniques, including both analog and digital lock-in amplifiers to demodulate the cantilever oscillation at any desired frequency. Note also, that while the highest amplitude responses will occur at mode resonances, it is possible to use frequencies that are off resonance or even between resonances if sufficient signal level permits measurements of the cantilever motion. Note that it is possible to measure the cantilever deflections at multiple mode simultaneously. Thus there is no increase in measurement time required to employ the multifrequency spectral demixing algorithms of the current invention.

Often the component spectra $A(\lambda)$ and $B(\lambda)$ are not known. In fact a key goal of AFM-IR techniques is to determine the sample absorption spectrum $A(\lambda)$ with high spatial resolution on samples of unknown composition and/or morphology. To achieve this, the inventors applied techniques to mathematically decompose the set of mode spectra $S_n(\lambda)$ into components corresponding to signal of interest $A(\lambda)$ and unwanted background $B(\lambda)$. With a sufficient number of mode spectra it is possible to decompose with significant confidence the component spectra $A(\lambda)$ and $B(\lambda)$ and component weighting factors $a_n$ and $b_n$.

The inventors have appreciated that multivariate demixing techniques may be applied to this problem. The inventors identified one technique known as multivariate curve resolution (MCR) as especially suitable for decomposing multifrequency responses into component spectra for the sample and background. The MCR technique is also called self-modeling mixture analysis and a variety of other names. These techniques have been applied to conventional infrared spectroscopy, for example, on mixed materials, where the observed spectra are a linear combination of the sub-component spectra, scaled by the relative concentration of different sub-components. For this type of analysis, however, it is necessary to make many measurements taken at different concentrations of the sub-components, or in the case of microscopy, at many different locations of the sample. For a single measurement, for example at a single concentration or single point on a sample, it has generally not been possible to decompose such spectra into subcomponents without prior knowledge of the sub-component spectra. Thus application of MCR in the prior art has involved very time-consuming procedures, e.g. to measure absorption spectra sequentially at a significant number of sub-component concentration or at a number of different locations on a sample.

In the case of the current invention, the inventors demonstrated that it is possible to rapidly and automatically extract the sample absorption spectrum at individual points on a sample, i.e. without the requirement to measure the sample at different locations or at different component concentrations. This is achieved for example by simultaneously observing the probe response at different cantilever mode frequencies. Instead of acquiring multiple spectra under different conditions, the current invention allows spectra to be demixed from a measurement at a single location on a sample. This is achieved by using the differentiated response to background and sample absorption for each cantilever oscillation mode, as discussed above. These different mode spectra can be acquired simultaneously and at the same location, with no increase in measurement time. Thus the current invention enables the ability to calculate separate background and sample absorption spectra, even with a single spectroscopic measurement, i.e. a single sweep across a range of wavelengths at a single location on a sample. This is a significant advance over conventional spectral demixing techniques which generally require measurements at multiple points on a sample or multiple concentrations of sub-components.

In one embodiment, multivariate curve resolution can be used to decompose the probe response at multiple frequencies and wavelengths into signal and background components. Multivariate curve resolution employs matrix methods to decompose a collection of absorption spectra into a matrix multiplication of component spectra and weighting factors. For a family of measured spectra, in our case the mode spectra $S_n(\lambda)$ are assembled into a data matrix D. The spectral demixing technique attempts to find a weighting vector W and a matrix of component spectra $S_c$, such that $$D = W \cdot S_c^T; \text{ (where the } T \text{ superscript indicates a matrix transposition)}. \quad \text{(Eq. 5)}$$

A variety of matrix and optimization techniques can be used to find optimal combinations of the weighting factors W and component spectra $S_c$. Note that in general the mathematical solution may not be unique. But by applying a variety of real world constraints, for example that the component spectra and the weightings must be non-negative, and other constraints, convergent solutions can be found.

Other techniques that can be used for similar spectral decomposition include alternating least squares analysis, band-target entropy minimization, and other chemometric, spectral demixing techniques.

Now that the reconstruction technique has been detailed, we return to the results of this invention. FIG. 3 shows a spectrum derived in the bottom up configuration (dashed line) which is not subject to the effects of background illumination and is considered an acceptable measurement. This spectrum agrees well with bulk FTIR spectra derived for bulk measurements (not shown). Also shown is a corresponding spectrum derived from the top down configuration (solid line). As can be seen, the top down spectrum is noisy, distorted, and does not correlate well with the bottom up spectrum. After application of the current invention, (FIG. 4) good agreement can be achieved in top down illumination. The top down spectrum in FIG. 4 was constructed using the multi-frequency reconstruction process described above, specifically using multivariate curve resolution applied to the cantilever oscillation amplitude versus wavelength for the first six cantilever contact resonance modes. As can be seen the agreement between top down and bottom up is very good and significantly improved over the top down data from FIG. 3.

It is also possible to apply simpler techniques to construct spectra that can substantially suppress background contributions. For example, it is possible to manually construct a spectrum that is a superposition of the responses at different cantilever modes. The inventors have used, for example, the following construction:

$$A(\lambda)=c_n S_n(\lambda)-c_1 S_1(\lambda);\qquad\text{(Eq. 6)}$$

where $A(\lambda)$ is the reconstructed sample spectrum, $S_n(\lambda)$ is the spectrum measured at a higher order nth mode, $S_1(\lambda)$ is the spectrum of the $1^{st}$ mode, and $c_n$ and $c_1$ are weighting coefficients. This construction can produce favorable results because the contribution of the background is generally highest in the $1^{st}$ mode and lower in higher order modes. So subtracting the first mode response from a higher mode response can in many cases substantially reduce the background. The weighting coefficients $c_n$ and $c_1$ can be determined in a variety of ways. For example, they can be determined on a reference material with a known spectroscopic response. The weighting coefficients can be adjusted such that $A(\lambda)$ best matches a known spectrum for the reference sample. Alternately, they can be adjusted such that the baseline values of the spectrum $A(\lambda)$ are as low as possible without being negative, i.e. constrained by the real world limit that absorptions must be positive. Note that for relative spectra, i.e. where the absorption measurement is made in arbitrary or normalized units, it is necessary to only adjust the ratio of the two weighting coefficients. It is also possible to create spectra with more generalized constructions, e.g.

$$A(\lambda)=\Sigma c_n S_n(\lambda);\qquad\text{(Eq. 7)}$$

where $S_n(\lambda)$ are the absorption spectra measured at each nth cantilever oscillation mode and $c_n$ are weighting coefficients. In general such a linear combination of mode spectra can be used to successfully reconstruct sample spectra, but of course more complicated nonlinear constructions can also be used if desired, especially in the case of highly non-linear tip-sample interaction that could make a linear superposition non-ideal. These manual reconstruction techniques can be especially helpful in the case of limited sensitivity where for example only a smaller number of cantilever oscillation modes can be detected, and/or conditions where the multivariate analyses do not readily converge on their own. In a hybrid approach, multivariate techniques like MCR can be performed on one sample and the resulting weighting coefficients $c_n$ can be used to manually reconstruct spectra on other samples or other regions of the sample.

Figure 9:
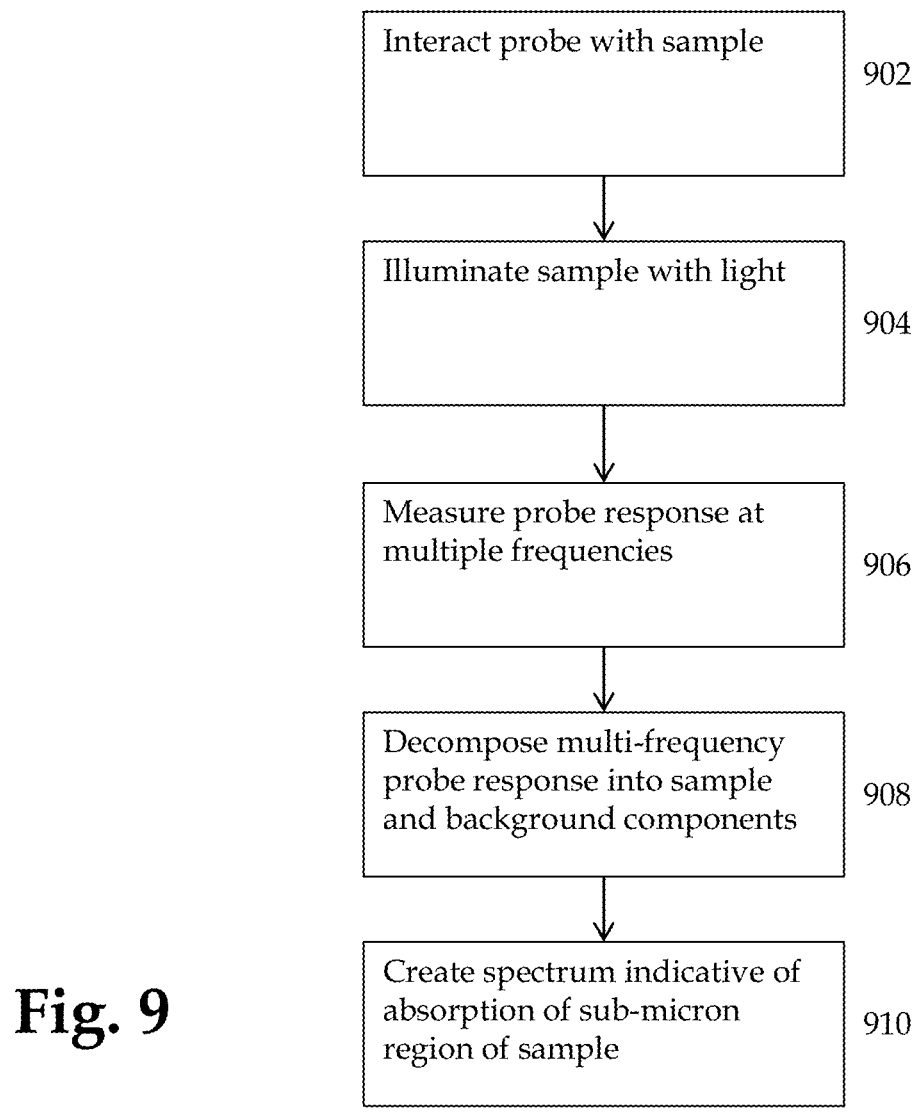
FIG. 9 is a flow chart of a novel method according to the invention.

FIG. 9 is a flow chart of one method of the current invention. In the first step 902, the AFM probe is interacted with the sample surface. This interaction can include contact mode, non-contact, tapping, intermittent contact or other interaction mode that results in the AFM probe sensing a response from the sample surface. In the second step 904, the sample is illuminated with light from a source of interest. In one embodiment, this source is a source of infrared radiation, such as an optical parametric oscillator and/or quantum cascade laser. It may also be another form of infrared laser, a broadband laser source, a thermal source or any other source that produces radiation that can be directed towards the sample in the vicinity of the AFM tip. In the next step 906, the probe response is measured in response to the incident radiation. The probe response may be due to thermal expansion of the sample due to absorption of radiation. It may also be due to forces induced on the AFM tip due to polarization of the tip and sample from the incident radiation or any alternate mechanism by which the incident radiation is transduced into a force between the tip and sample. The probe response is then analyzed at a plurality of frequencies. These frequencies may correspond to contact resonance modes, free/tapping resonance modes, or at an arbitrary collection of frequencies. In the next step 908 the multi-frequency cantilever response is decomposed into separate absorption components, for example corresponding to absorption by the sample absorption and background absorption. In the final step 910, an absorption of a sub-micron region of the sample is constructed by recording and/or plotting one or more of the sample absorption components as a function of wavelength, radiation frequency (e.g. wavenumber) or an equivalent spectroscopic parameter. Note that these steps do not necessarily need to be performed in the order indicated and steps can be either separated into further sub-steps or combined such that multiple steps occur together.

Figure 10:
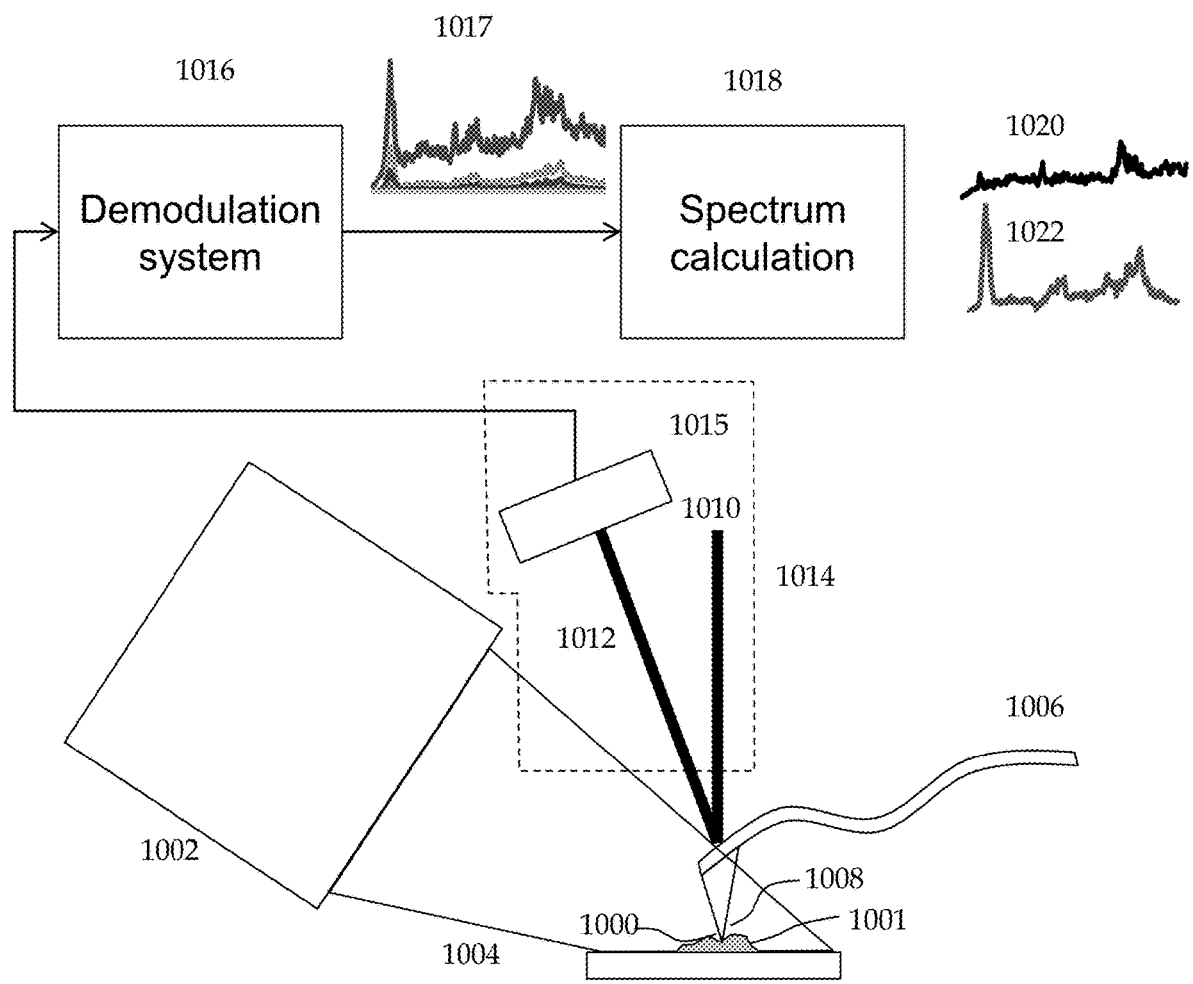
FIG. 10 is a simplified schematic diagram of an apparatus under the current invention.

FIG. 10 shows an apparatus under an embodiment of the current invention. Cantilever probe 1006 with tip 1008 is illuminated with a beam of radiation 1004 from radiation source 1002. The beam of radiation 1004 is incident on a region of interest 1000 of a sample 1001. A portion of the beam 1004 is also often incident on a portion of the tip 1008, potentially a portion of the cantilever 1006 and regions of the sample away from the tip apex. When radiation is absorbed by the sample and/or cantilever probe, the absorbed radiation induces a detectable probe response. The probe response can include a temperature rise, a transient motion, a steady state oscillation, a force, a force gradient or other responses. In one embodiment, the absorbed radiation generates heat in the sample that causes thermal expansion of the sample. The resulting thermal expansion of the sample can induce motion in the cantilever probe 1006. The oscillation can be transient, for example a rapid rise and then decaying oscillatory behavior. It can also be a continuous oscillation, for example if the radiation source is pulsed or modulated periodically, for example at one or more resonances of the cantilever 1006.

The response of the cantilever probe is detected by probe response detection system 1014. In many cases this is an optical lever system, used to measure the motion, position, deflection and/or displacement of the cantilever probe. A simple embodiment is for example a light beam 1010 incident on the cantilever 1006 and reflected beam 1012 directed to a position sensitive photodetector 1015. The probe response detection system may comprise many other more complex systems for measuring cantilever motion or position, including optical interferometers, inductive/capacitive sensors, thermal detection and/or any system that transduces the cantilever position/motion into a detectable signal. The probe response detection system can alternately detect other probe responses, for example temperature, temperature rise, force, force gradient or other probe responses. The source of radiation 1002 can be one of many sources. It can be a laser, laser diode, optical parametric oscillator, optical parametric generator, broadband light source, supercontinuum source, nanosecond, picosecond or femtosecond laser, a super continuum laser, a frequency comb device, a quantum cascade laser, a thermal source, any combination of the above or any other light source that can be directed towards the probe and create a detectable probe response. The radiation source may operate over any wavelength range of interest, including but not limited to visible, infrared, ultraviolet, terahertz, and x-ray. The radiation source is also tunable over some range such that wavelength dependent spectroscopic information can be determined from the sample. In one embodiment the radiation source is an infrared laser with a tuning range within the mid-infrared, for example within the range 2.5-15 µm.

A beam of radiation 1004 from the source 1002 is generally focused in the vicinity of the tip 1008 of the probe 1006. The focusing can be accomplished by refractive, reflective and/or diffractive optics in any combination. In one embodiment the focusing optics comprises a lens and/or an off-axis parabolic mirror with an effective focal length between 25-100 mm. There may also be a wide variety of other components (not shown) included within the source of radiation 1002 or between the source and the output beam 1004. For example there may be polarizers, attenuators, flat mirrors, beam steering mirrors, apertures, etc. Note also that FIG. 10 is a simplified schematic and is not drawn at all to scale.

Once the probe response to the incident radiation is transduced by the probe response detection system 1014, the output signal is sent to the demodulation system. The signal can be transmitted via analog and/or digital means. Within the demodulation system, the probe response is analyzed at a plurality of frequencies. As the source of radiation is tuned across different wavelengths, the demodulation system 1016 produces signals indicative of the probe response at the plurality of frequencies and wavelengths (1017). These signals can also be analog or digital. The demodulation can be accomplished via lock-in amplifier (digital and/or analog), Fourier transform, discrete Fourier sums at selected frequencies, wavelet analysis, or any other technique that produces a signal that is indicative of the probe response at the desired frequencies. The demodulation system can also automatically select the frequencies at which to demodulate and/or measure, for example by performing a Fourier analysis on the probe response and selecting the highest peaks above a desired threshold level. The demodulation may also employ non-sinusoidal demodulation (e.g. employing transforms with non-sinusoidal basis functions).

Next the wavelength and frequency dependent outputs of the demodulation system are sent to a computation system 1018 that decomposes the multi-frequency probe response into signal 1022 and background components 1020, in which the signal component comprises spectroscopic information about the sub-micron region of the sample. The computation system may be a personal computer, a digital signal processor, a field-programmable gate array and/or other digital electronics that are capable of executing the desired decomposition algorithm. The decomposition algorithm can comprise any of the algorithms mentioned previously, for example multivariate curve resolution, self-modeling mixture analysis, spectral demixing, band target entropy minimization, and alternating least squares, and other related techniques. In one embodiment the output of the decomposition algorithm is an infrared absorption spectrum of a sub-micron region of a sample for material in the vicinity of the apex of cantilever probe tip 1008. For simplicity in this application we have referred in many places to spectra or spectroscopic measurements as a function of the wavelength of the radiation source. Note that many spectra are measured and/or displayed as a function of optical frequency (e.g. wavenumber in cm-1) rather than as a function of wavelength. Whenever a measurement is described in this patent application and associated claims as a function of wavelength, it is understood that the measurement can equivalently be performed/displayed alternately as a function of optical frequency/wavenumber.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for obtaining spectroscopic information about a sub-micron region of a sample on a sample mount using an atomic force microscope, the method comprising:
    a) Interacting a probe of the atomic force microscope (AFM) with the sub-micron region of the sample;
    b) Illuminating the sample with a top down beam of radiation;
    c) Measuring a response of the AFM probe due to absorption of incident radiation at a plurality of radiation wavelengths;
    d) Determining the AFM probe response at a plurality of AFM probe oscillation frequencies;
    e) Decomposing the AFM probe response at the plurality of AFM probe oscillation frequencies into sub-micron sample region components at about an apex of a tip of the probe, and background components, and use the sub-micron sample region components to calculate spectroscopic information about the sub-micron region of the sample, wherein the background components are caused by absorption of the radiation by at least one of a cantilever of the probe, part of the tip of the probe away from the tip apex, and a region of the sample away from the tip apex; and
    f) Storing a representation of the spectroscopic information on a machine readable medium.

2. The method of claim 1 wherein the combining step comprises subtracting a scaled response at a frequency corresponding to a fundamental cantilever resonance mode from the probe response at a frequency corresponding to a higher order resonance mode.

3. The method of claim 1 wherein the combining step comprises decomposing the probe response at a plurality of frequencies and wavelengths into multiple component spectra.

4. The method of claim 3 wherein the component spectra comprise at least a background response and a response originating from the sub-micron region.

5. The method of claim 3 wherein decomposing the probe response comprises applying at least one of: multivariate curve resolution, self-modeling mixture analysis, band target entropy minimization, spectral demixing, and alternating least squares.

6. The method of claim 1 wherein the spectroscopic information comprises a spectrum indicative of wavelength dependent absorption of the sub-micron region.

7. The method of claim 1 wherein the plurality of frequencies correspond to cantilever resonance modes.

8. The method of claim 7 wherein the cantilever oscillation modes are comprised of at least one of: contact resonance modes, free resonance modes, and tapping resonance modes.

9. The method of claim 1 wherein the probe response at the plurality of frequencies is decomposed into component spectra and component weighting factors.

10. The method of claim 1 wherein the illumination is top down illumination.

11. The method of claim 1 wherein the sample is substantially opaque to infrared light.

12. The method of claim 1 wherein the sample comprises an in-situ sample.

13. A method for obtaining spectroscopic information about a sub-micron region of a sample using an atomic force microscope, the method comprising:
   a) Interacting a probe of the atomic force microscope (AFM) with the sub-micron region of the sample;
   b) Illuminating the sample with a beam of radiation, at least a portion of the radiation incident on the sub-micron region of the sample;
   c) Measuring a response of the probe due to absorption of incident radiation;
   d) Determining the AFM probe response at or near a plurality of probe oscillation mode frequencies;
   e) Applying at least one of multivariate curve resolution, self-modeling mixture analysis, spectral demixing, and alternating least squares to the AFM probe response at a plurality of AFM probe oscillation frequencies to decompose the AFM probe response into a background response component and a component from the response from the sub-micron region of the sample;
   f) Producing a measurement of spectroscopic information of the sub-micron region of the sample resulting from the sub-micron sample region component; and
   g) Storing a representation of the spectroscopic information on a machine readable medium.

14. The method of claim 13 wherein the spectroscopic information comprises an absorption spectrum.

15. The method of claim 13 wherein the beam of radiation comprises a radiation from a pulsed infrared source.

16. The method of claim 13 wherein the plurality of frequencies correspond to multiple resonance modes of the cantilever.

17. The method of claim 16 wherein the resonance modes comprise of at least one of: contact resonance modes, free resonance modes, and tapping resonance modes.

18. The method of claim 13 wherein the illumination is top down illumination.

19. The method of claim 13 wherein the sample is substantially opaque to infrared light.

20. The method of claim 13 wherein the sample is an in situ sample.

21. An apparatus for measuring spectroscopic information from a sub-micron region of a sample with a probe microscope (PM), the apparatus comprising:
   a) a source of radiation that is directed towards a region of a sample in proximity to a probe of the probe microscope;
   b) a PM probe response detection system that measures a signal indicative of a response of the probe of the probe microscope to radiation incident on the sample;
   c) a demodulation system that decomposes the signal indicative of the probe response at a plurality of PM probe oscillation frequencies into a background component and probe proximity component;
   d) a computation system that applies an algorithm to combine the probe proximity component response at the plurality of PM probe oscillation frequencies to calculate spectroscopic information about the sub-micron region of the sample.

22. The apparatus of claim 21 wherein the source of radiation emits infrared radiation including at least a portion emitted within a wavelength range between 2.5 to 15 μm.

23. The apparatus of claim 21 wherein the source of radiation comprises at least one of an optical parametric oscillator, and a quantum cascade laser.

24. The apparatus of claim 21 wherein the source of radiation comprises at least one of broadband laser, a super continuum laser, a femtosecond laser, a frequency comb laser, and a thermal source.

* * * * *